United States Patent [19]

Yamamoto et al.

[11] 4,387,219
[45] Jun. 7, 1983

[54] 2-HYDROXY GENTAMICIN COMPOUNDS

[75] Inventors: Haruo Yamamoto, Chigasaki, Japan; Sol J. Daum, Albany, N.Y.

[73] Assignee: Sterling Drug Inc., New York, N.Y.

[21] Appl. No.: 209,412

[22] Filed: Nov. 24, 1980

Related U.S. Application Data

[62] Division of Ser. No. 93,062, Nov. 13, 1979, Pat. No. 4,288,547.

[51] Int. Cl.$^3$ ............................................. C07H 15/22
[52] U.S. Cl. .................................... 536/13.6; 424/180; 536/16.8
[58] Field of Search .................... 536/17 R, 13.6, 16.8

[56] References Cited

U.S. PATENT DOCUMENTS

| | | | |
|---|---|---|---|
| 3,780,018 | 12/1973 | Konishi et al. | 536/17 |
| 3,903,072 | 9/1975 | Ilavsky et al. | 536/13.6 |
| 3,915,955 | 10/1975 | Cooper et al. | 536/13.6 |
| 3,972,930 | 8/1976 | Daum et al. | 536/17 |
| 3,982,996 | 9/1976 | Daum et al. | 536/13.6 |
| 4,000,261 | 12/1976 | Daniels | 536/13.6 |
| 4,028,188 | 6/1977 | Daum et al. | 536/17 |
| 4,044,123 | 8/1977 | Daniels et al. | 536/17 |
| 4,055,715 | 10/1977 | Tomioka et al. | 536/17 |
| 4,117,221 | 9/1978 | Daniels | 536/13.6 |

*Primary Examiner*—Johnnie R. Brown
*Attorney, Agent, or Firm*—William G. Webb; B. Woodrow Wyatt

[57] ABSTRACT

2-Hydroxygentamicins B, $B_1$ and $A_3$ and 2-hydroxy antibiotics JI-20A and JI-20B are prepared as fermentation products by culturing a nutrient medium containing carbohydrates, a source of assimilable nitrogen, essential salts and D-streptamine with a mutant of *Micromonospora purpurea*, and isolating the said fermentation products from the nutrient medium; the fermentation products are acylated with an ester of an ω-(N-benzyloxycarbonyl)amino-α-hydroxy-lower-alkanoic acid, after first blocking the 6'-and/or 2'-amine group with an amine-protecting group, followed by catalytic hydrogenolysis of the benzyloxycarbonyl group and removal of the amine-protecting groups to prepare the 1-N-(ω-amino-α-hydroxy-lower-alkanoyl) derivatives.

6 Claims, No Drawings

2-HYDROXY GENTAMICIN COMPOUNDS

RELATED APPLICATIONS

This is a division of our copending application Ser. No. 93,062, filed Nov. 13, 1979, now U.S. Pat. No. 4,288,547, patented Sept. 8, 1981.

BACKGROUND OF THE INVENTION (a) Field of the Invention

This invention relates to aminocyclitol antibiotics of the gentamicin class, which are useful as antibacterial agents.

(b) Description of the Prior Art

Daum et al., U.S. Pat. No. 3,972,930 discloses 2-hydroxygentamicins $C_1$, $C_2$ and $C_{1a}$ which are prepared in a fermentative process involving the incorporation of D-streptamine into the products using a particular mutant of *Micromonospora purpurea*, namely *M. purpurea* ATCC 31,119, and Daum et al., U.S. Pat. No. 3,982,996 discloses the fermentative process for the preparation of the same 2-hydroxygentamicin components involving the incorporation of either D-streptamine or certain non-nitrogen containing cyclitols, for example scyllo-inosose or scyllo-inosose pentaacetate, using a further mutant of *M. purpurea* ATCC 31,119, namely *M. purpurea* ATCC 31,164. However, these patent disclosures do not describe the preparation of 2-hydroxygentamicins B, $B_1$ and $A_3$ and 2-hydroxy antibiotics JI-20A and JI-20B, which are disclosed and claimed herein, and moreover to date these compounds have not been isolated from or detected in the fermentation products obtained by the Daum et al. procedures disclosed in these two patents.

Cooper et al., U.S. Pat. No. 3,915,955 discloses gentamicins B and $B_1$; Ilasky et al., U.S. Pat. No. 3,903,072 disclose antibiotics JI-20A and JI-20B; and Daniels et al., U.S. Pat. No. 4,000,261 disclose epi-gentamicins B, $B_1$ and $A_3$ and epi-antibiotics JI-20A and JI-20B.

Daniels, U.S. Pat. No. 4,117,221 discloses certain N-(ω-amino-α-hydroxy-lower-alkanoyl) derivatives of gentamicins $C_1$ and B.

SUMMARY OF THE INVENTION

In a composition of matter aspect, this invention relates to certain 2-hydroxygentamicins, specifically 2-hydroxygentamicins B, $B_1$ and $A_3$ and 2-hydroxy antibiotics JI-20A and JI-20B, and to 1-N-(ω-amino-α-hydroxy-lower-alkanoyl) derivatives thereof.

In a process aspect, the invention relates to a process for preparing the said 2-hydroxygentamicins B, $B_1$ and $A_3$ and 2-hydroxy antibiotics JI-20A and JI-20B as fermentation products which comprises culturing a nutrient medium containing carbohydrates, a source of assimilable nitrogen, essential salts and D-streptamine with *M. purpurea* ATCC 31,536 and isolating the said fermentation products.

In a second process aspect, the invention relates to a process for preparing the said 1-N-(ω-amino-α-hydroxy-lower-alkanoyl) derivatives of 2-hydroxygentamicins B, $B_1$ and $A_3$ and 2-hydroxy antibiotics JI-20A and JI-20B which comprises reacting 2-hydroxygentamicins B, $B_1$ or $A_3$ or 2-hydroxy antibiotics JI-20A or JI-20B with an acylating agent in order to derivatize the starting material at the 2'- and the 6'-amine groups with an amine-protecting group; reacting the product with an N-hydroxysuccinimide ester of an ω-(N-benzyloxycarbonyl)amino-α-hydroxy-lower-alkanoic acid; subjecting the product to catalytic reduction to effect hydrogenolysis of the benzyloxycarbonyl group in the resulting product; and hydrolysis of the 2'- and 6'-amine-protecting groups.

DETAILED DESCRIPTION INCLUSIVE OF THE PREFERRED EMBODIMENTS

More specifically, this invention relates to compounds having one of the formulas:

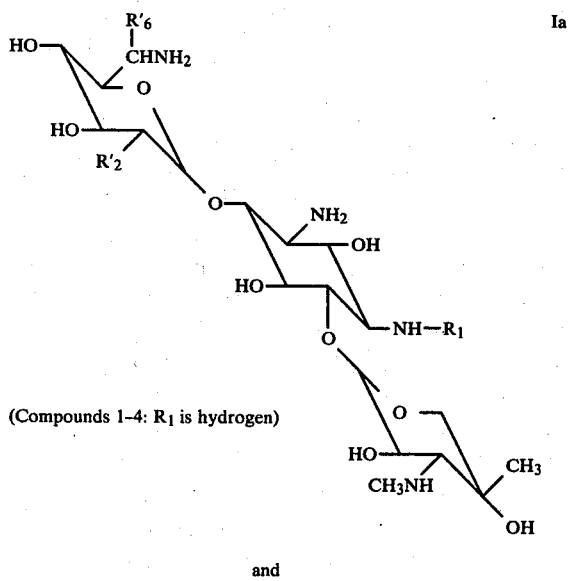

(Compounds 1-4: $R_1$ is hydrogen)

and

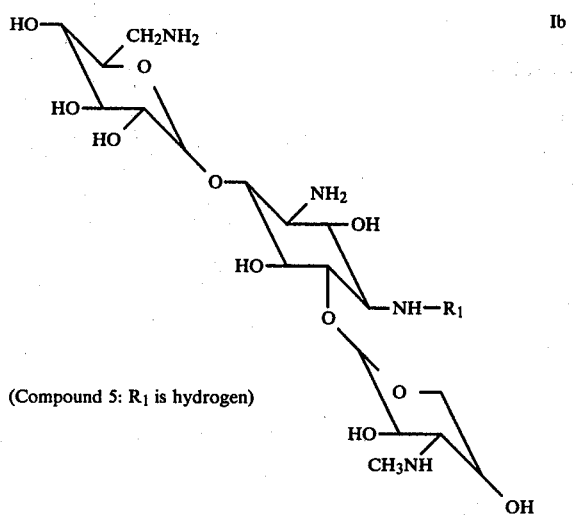

(Compound 5: $R_1$ is hydrogen)

where $R_1$ is hydrogen or an ω-amino-α-hydroxy-lower-alkanoyl group having the formula:

where n is one of the integers 1 or 2; and where, in formula Ia, $R_2'$ is hydroxy or amino and $R_6'$ is hydrogen or methyl.

As indicated above, the compounds of the invention embraced by formula Ia above where $R_1$ in each case is hydrogen are designated herein as Compounds 1-4 as follows where:

Compound 1: $R_2'$=OH; $R_6'$=H
Compound 2: $R_2'$=OH; $R_6'$=$CH_3$

Compound 3: $R_2'=NH_2$; $R_6'=H$

Compound 4: $R_2'=NH_2$; $R_6'=CH_3$ and the compound of formula Ib where $R_1$ is hydrogen is designated herein as Compound 5.

The compounds of formulas Ia and Ib are chemically designated as: O-[3-deoxy-4-C-methyl-3-methylamino-β-L-arabinopyranosyl-(1→6)]-O-[6-amino-6-deoxy-α-D-erythroglucopyranosyl-(1→4)]-D-streptamine (Compound 1); O-[3-deoxy-4-C-methyl-3-methylamino-β-L-arabinopyranosyl-(1→6)]-O-[6-amino-6-C-methyl-6-deoxy-α-D-erythro-glucopyranosyl-(1→4)]-D-streptamine (Compound 2); O-[3-deoxy-4-C-methyl-3-methylamino-β-L-arabinopyranosyl-(1→6)]-O-[2,6-diamino-2,6-dideoxy-α-D-erythro-glucopyranosyl-(1→4)]-D-streptamine (Compound 3); O-[3-deoxy-4-C-methyl-3-methylamino-β-L-arabinopyranosyl-(1→6)]-O-[2,6-diamino-6-C-methyl-2,6-dideoxy-α-D-erythro-glucopyranosyl-(1→4)]-D-streptamine (Compound 4); and O-[3-deoxy-3-methylamino-β-L-arabinopyranosyl-(1→6)]-O-[6-amino-6-deoxy-α-D-erythro-glucopyranosyl-(1→4)]-D-streptamine (Compound 5). However, for the sake of brevity, these compounds will hereinafter be identified, respectively, as:

Compound 1: 2-hydroxygentamicin B
Compound 2: 2-hydroxygentamicin $B_1$
Compound 3: 2-hydroxy antibiotic JI-20A
Compound 4: 2-hydroxy antibiotic JI-20B
Compound 5: 2-hydroxygentamicin $A_3$ The compounds of formulas Ia and Ib where $R_1$ is hydrogen are prepared by the method described in Shier et al., U.S. Pat. No. 3,669,838, which comprises culturing a nutrient medium containing carbohydrates, a source of assimilable nitrogen, essential salts and D-streptamine with a mutant of *Micromonospora purpurea*, namely *M. purpurea* ATCC 31,536, which is a mutant of *M. purpurea* ATCC 31,164 disclosed in Daum et al. U.S. Pat. No. 3,982,996, and isolating the product from the culture medium. In accordance with the procedure described by Shier et al., the nature of the mutant is such that it is incapable of synthesizing the D-streptamine subunit from a nutrient medium in order to thereby produce the antibiotic, but is capable of incorporating D-streptamine into an antibiotic when the D-streptamine is added to the nutrient medium.

The compounds of formulas Ia and Ib where $R_1$ represents an ω-amino-α-hydroxy-lower-alkanoyl group are prepared by the method described by Daniels, U.S. Pat. No. 4,117,221. This method comprises reacting a compound of formula Ia or Ib with an acylating agent in order to derivatize the starting material at the 2'- and 6'-amine groups with an amine-protecting group, for example the trifluoroacetyl, t-butoxycarbonyl or benzyloxycarbonyl group, followed by reaction of the resulting derivative with an N-hydroxysuccinimide ester having the formula II:

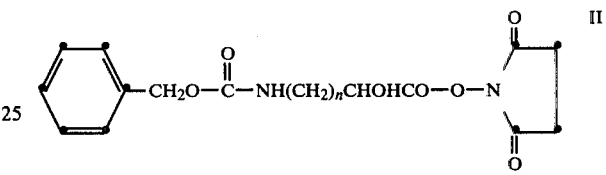

where n has the meanings given above.

The products thus obtained are then subjected to hydrogenolysis with hydrogen over a catalyst in order to effect removal of the benzyloxycarbonyl group, and in a final step, the amine-protecting group is removed by hydrolysis with trifluoroacetic acid.

The reaction sequence, where use of the t-butoxycarbonyl group as the amine-protecting group is illustrated, is represented as follows:

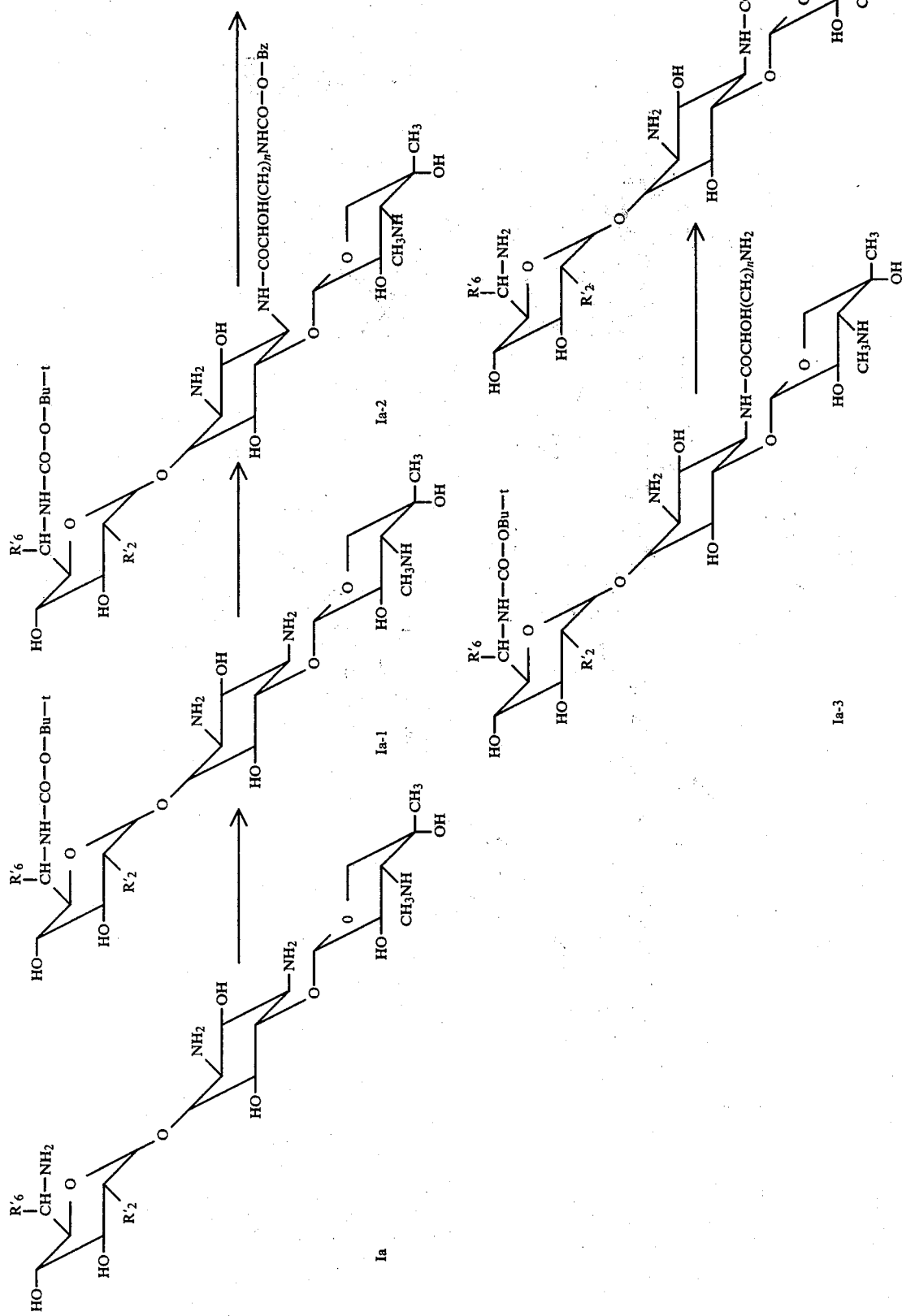

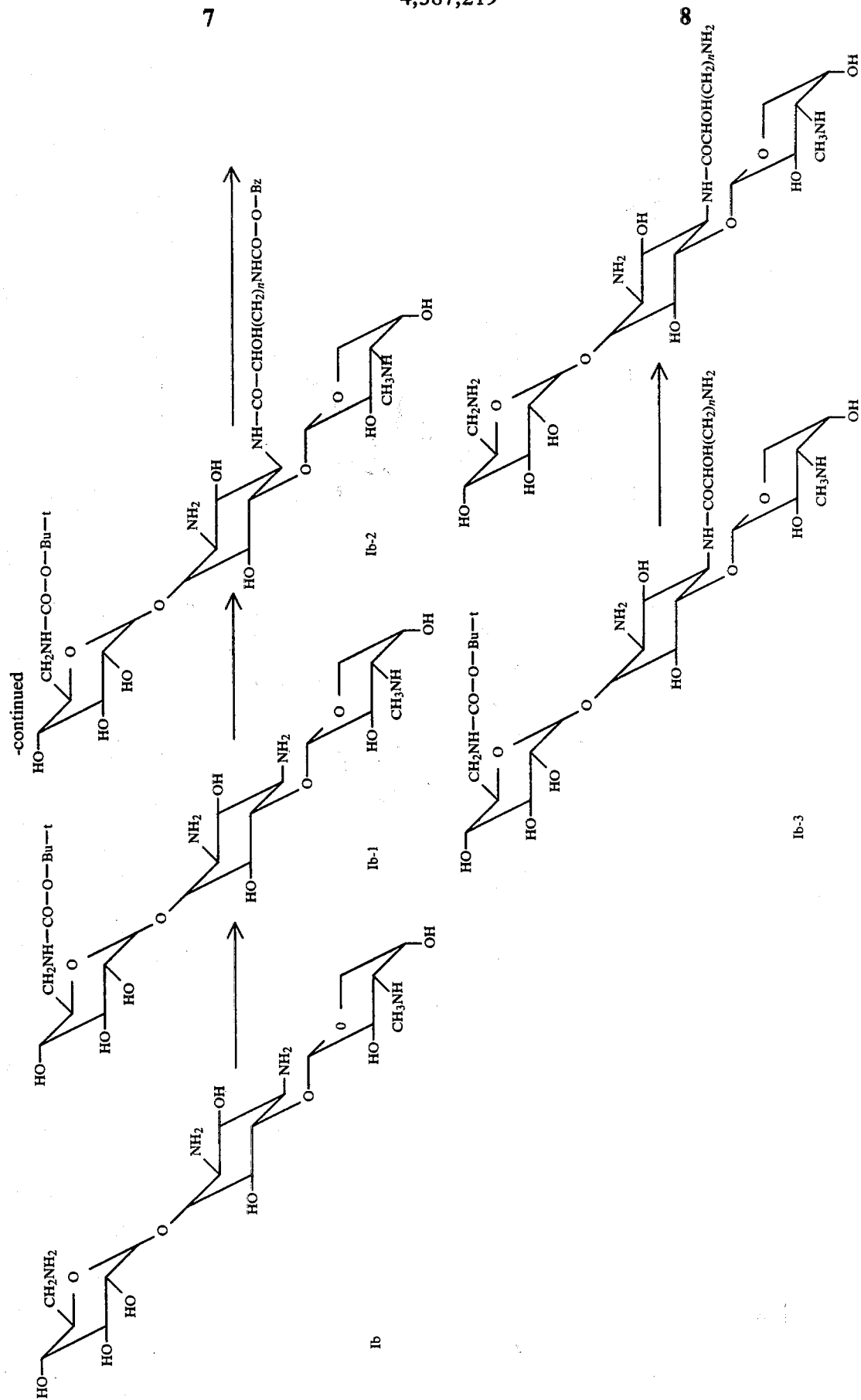

where the symbols t—BuO—CO— and BzO—CO— represent, respectively, the t-butoxycarbonyl and benzyloxycarbonyl groups, and $R_2'$, $R_6'$ and n have the meanings given above.

The 6'-t-butoxycarbonyl derivatives of formulas Ia-1 and Ib-1 above are prepared by reaction of a compound of formula Ia or Ib with t-butyl S-(4,6-dimethylpyrimidin-2-yl) thiolcarbonate in the presence of a molar excess of an acid acceptor, for example a tri-lower-alkylamine. The reaction is carried out in an aqueous solution of an inert organic solvent, for example tetrahydrofuran, dioxane, dimethylformamide and the like, preferably at a temperature of 0°–20° C. During the course of the reaction, any other primary amine group in the erythro-glucopyranosyl ring, for example the 2'-amino group in 2-hydroxy antibiotics JI-20A and JI-20B (Compounds 3 and 4), would also react with the t-butyl thiolcarbonate reagent, and in such cases two molar equivalents of the latter reagent would be used. The amine-protecting groups at the 2'- and 6'-positions would then be removed simultaneously in the last step as described hereinbelow.

The 1-N-(ω-amino-α-hydroxy-lower-alkanoyl) derivatives of formulas Ia-2 and Ib-2 above are prepared by reaction of a compound of formula Ia-1 or Ib-1 with a molar equivalent amount of an N-hydroxysuccinimide ester of formula II, preferably at a temperature from −10° C. to about 10° C., in an aqueous solution of an inert organic solvent, for example tetrahydrofuran, dioxane, ethyleneglycol dimethyl ether, dimethylacetamide, dimethylformamide, propyleneglycol dimethyl ether and the like.

Hydrogenolysis of the benzyloxycarbonyl group in the compounds of formulas Ia-2 and Ib-2 above is carried out over a palladium-on-charcoal catalyst in an inert, water miscible organic solvent, for example, methanol, ethanol, dioxane, tetrahydrofuran, ethyleneglycol dimethyl ether, propyleneglycol dimethyl ether and the like.

Hydrolysis of the amine-protecting group (e.g. the t-butoxycarbonyl group) in the compounds of formulas Ia-3 and Ib-3 above is carried out by dissolving the compound of formula Ia-3 or Ib-3 in trifluoroacetic acid at ambient temperature. If desired, the product can be isolated in the form of the trifluoroacetate salt by dilution of the reaction mixture with diethyl ether, and the salt can, in turn, be converted to the free base form, preferably by passing an aqueous solution of the salt form over a basic ion exchange resin in the hydroxide ion form and lyophilizing the aqueous solution thus produced.

Due to the presence of basic amino groupings, the free base forms represented by formulas Ia and Ib above react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, α-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indole acetic acid, barbituric acid, sulfamic acid, methanesulfonic acid, ethanesulfonic acid, isethionic acid, benzenesulfonic acid, 4-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid and the like.

All of the acid-addition salts are useful as sources of the free base forms by reaction of the salts with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic, pharmaceutically acceptable acids, for example, sulfuric acid, hydrochloric acid, lactic acid, tartaric acid and the like, are of course employed.

The compounds of formulas Ia and Ib have been tested in a standard serial dilution antibacterial test and have been found to have antibacterial activity. The compounds are thus useful as antibacterial agents.

The compounds of formulas Ia and Ib are primarily intended for oral, topical or parenteral administration and can be prepared for use by suspension, either in the form of their free bases or as pharmaceutically acceptable non-toxic acid-addition salts, in an inert carrier such as polyethyleneglycol, or by tabletting or encapsulation for oral administration either alone or with suitable adjuvants, or alternatively they can be formulated with conventional creams or jellies for topical application.

The molecular structures of the compounds of the invention were assigned on the basis of their method of preparation; by study of their chromatographic characteristics determined by thin layer chromatographic (tlc) analyses; by their nuclear magnetic resonance (nmr) and mass spectra; by the correspondence between calculated and found values for elementary analyses for the elements; and by acid hydrolysis and study of the chromatographic characteristics of the degradation products thereby obtained.

The following specific examples are illustrative of the manner of making the compounds of the invention.

EXEMPLARY DISCLOSURE

A. Incorporation of D-Streptamine and Isolation of the Products

EXAMPLE 1

The mutant organism, *M. purpurea* ATCC 31,536, which was obtained as a mutant of *M. purpurea* ATCC 31,164 using the mutation procedures described in U.S.

Pat. No. 3,972,930, was maintained on N-Z amine agar slants in Medium 1 constituted as follows:

|  | g./l |
|---|---|
| Glucose | 10g. |
| Soluble starch | 20g. |
| Yeast extract | 5g. |
| N—Z—Amine-Type A (Difco) | 5g. |
| CaCO$_3$ | 1g. |
| Agar | 15g. |

A first stage seed was prepared by inoculating a loopful from the slant to 50 ml. of a germination medium (Medium 2) in a 250 ml. flask constituted as follows:

|  | g./l |
|---|---|
| Beef extract | 0.3% |
| Tryptone | 0.5% |
| Dextrose | 0.1% |
| Soluble starch | 2.4% |
| Yeast extract | 0.5% |
| CaCO$_3$ | 0.4% |

The culture was allowed to incubate for seventy-two hours at 28° C., and a 10% inoculum was then transferred to 50 ml. of Medium 2 in a 250 ml. flask. This was incubated for seventy-two hours as above. From this second stage seed a 10% inoculum was transferred to 500 ml. of Medium 2 in a 2 liter flask, and this was incubated for seventy-two hours at 28° C. A 10% inoculum from this third stage seed was transferred to 50 liters of Medium 2 in a 130 liter fermentor and sparged with filtered air at 50 liters/minute at 28° C. for seventy-two hours. Finally, a 5% inoculum from this tank stage seed was used to inoculate two 1 kiloliter fermentations using Medium 3 constituted as follows:

|  |  |
|---|---|
| Glucose | 2% |
| Soy bean meal | 0.75% |
| Difco yeast extract | 0.75% |
| CaCO$_3$ | 0.4% |
| CoCl$_2$.6H$_2$O | 0.0001% |
| Antifoam | 0.02% |
| Streptamine | 0.02% |

Fermentation was carried out at 28° C., and the tanks were sparged with filtered air for the first twelve hours at 500 liters/minute and at 800 liters/minute for the next one hundred fifty-two hours. (Total fermentation time one hundred sixty-four hours.)

The two fermentations were combined and adjusted to pH 2 with 18 N sulfuric acid and allowed to stand for one hour. The acidic broth was filtered through a filter press, and the filtrate (2 kiloliters) was adjusted to pH 7.4 with 6 N sodium hydroxide and passed over a column of Amberlite IRC 50 (ammonium ion form, 50 l.). The column was washed with 250 liters of water, and antibiotic material was eluted with 1 N ammonium hydroxide. The presence of antibiotic activity in the eluate was followed by bioautography against B. subtilis as challenge organism, and 76 liters of the eluate, having antibiotic activity, were concentrated in vacuo. The concentrate (3.7 l.) was passed over a column of Amberlite CG-50 (ammonium ion form, 20 l.) (Rohm and Haas, Philadelphia, Pa., 19105, U.S.A.). The column was washed first with 60 liters of water, and then with 20 liters of 0.25 N ammonium hydroxide. The eluate from the latter, on thin layer chromatography, was found to contain D-streptamine and a mixture of the compounds of formulas Ia and Ib. (If desired the major components, oxygentamicins C$_1$, C$_2$ and C$_{1a}$, which remain on the column following elution with 0.25 N ammonium hydroxide, can be eluted with 0.5 N ammonium hydroxide and isolated from the latter eluate in conventional fashion.) The D-streptamine was removed from the solution obtained by elution with 0.25 N ammonium hydroxide by concentration of the mixture to a small volume, addition of methanol and filtration to remove the D-streptamine which separated as crystals. The filtrate (800 ml.) was concentrated in vacuo to remove the methanol, and then was lyophilized. There was thus obtained 15 g. of a mixture of the compounds of formulas Ia and Ib as a brown powder.

The latter was dissolved in 150 ml. of water, the solution was neutralized with 1 N hydrochloric acid and passed through a column of Amberlite CG-50 (ammonium ion form, 750 ml.), and the column was washed first with 3750 ml. of water and then with 3750 ml. of 0.05 N ammonium hydroxide. Neither of these latter eluates were positive to ninhydrin and were discarded. Further elution of the column with 3750 ml. of 0.1 N ammonium hydroxide removed three ninhydrin positive compounds, none of which displayed antibiotic activity on challenge with B. subtilis, and the 0.1 N ammonium hydroxide eluate was thus discarded. The column was further eluted with 0.15 N ammonium hydroxide, a total of fifty-seven 150 ml. fractions being collected, and each fraction was assayed by thin layer chromatography and tested for antibiotic activity by challenge with B. subtilis. Certain of the fractions were combined and taken to dryness to give a total of six combined samples (hereinafter referred to as Combined Samples 1–6) constituted as follows:

| Combined Sample | Fractions | Amt. (mg.) |
|---|---|---|
| 1 | 9–15 | 1224 |
| 2 | 16–21 | 1915 |
| 3 | 22–27 | 612 |
| 4 | 28–37 | 2505 |
| 5 | 38–43 | 2405 |
| 6 | 44–57 | 3647 |

These combined samples were separately treated as described below in order to purify the compounds of the invention.

EXAMPLE 1(a)

Purification of Compound 1 (2-Hydroxygentamicin B)

Combined Sample 1, derived from original fractions 9–15 described above and comprising 1224 mg., was dissolved in 12 ml. of water, and the solution was neutralized with 1 N hydrochloric acid. The solution was passed over a column of Amberlite CG-50 resin (ammonium ion form, 65 ml.), and the column was washed first with 330 ml. of water and then eluted with 0.15 N ammonium hydroxide, the eluate being collected as 20 ml. fractions. Fractions 16–23, each of which showed a single spot on tlc, were combined, concentrated and lyophilized to give 632 mg. of 2-hydroxygentamicin B as the hemicarbonate.hemihydrate, m.p. 200° C., $[\alpha]_D^{20} + 156°$ (0.01% in water).

Anal. Calcd. for C$_{19}$H$_{38}$N$_4$O$_{11}$.½H$_2$CO$_3$.½H$_2$O: C, 43.49; H, 7.48; N, 10.40. Found: C, 43.42; H, 7.19; N, 10.08.

EXAMPLE 1(b)

Purification of Compound 2 (2-Hydroxygentamicin $B_1$)

Combined Sample 2 (1400 mg.), derived from original fractions 16–21 described above, was dissolved in 30 ml. of water, and the solution was neutralized with 1 N hydrochloric acid. The solution was passed over a column of Bio-Rex 63 resin (ammonium ion form, 70 ml., an intermediate acid cation exchange resin obtained from Bio-Rad Laboratories, 1205 South 32nd Street, Richmond, Calif., U.S.A.), and the column was washed first with 210 ml. of water and then eluted first with 840 ml. of 0.1 N ammonium hydroxide and then with 0.3 N ammonium hydroxide, 14 ml. fractions being collected. Fractions 45–60 were combined, concentrated and lyophilized to give 1052 mg. of 2-hydroxygentamicin $B_1$ as the carbonate.hemihydrate, m.p. 202° C., $[\alpha]_D^{20}+143°$ (0.01% in water).

Anal. Calcd. for $C_{20}H_{40}N_4O_{11}.H_2CO_3.\frac{1}{2}H_2O$: C, 43.22; H, 7.42; N, 9.69. Found: C, 43.50; H, 7.00; N, 9.32.

EXAMPLE 1(c)

Purification of Compound 5 (2-Hydroxygentamicin $A_3$)

Combined Sample 3 (600 mg.), derived from original fractions 22–27 described above, was dissolved in 6 ml. of water, the solution was neutralized with dilute hydrochloric acid and passed over a column of Bio-Rex 63 resin (ammonium ion form, 30 ml.), and the column was washed first with 150 ml. of water. The column was then eluted with 360 ml. of 0.1 N ammonium hydroxide, followed by 360 ml. of 0.3 N ammonium hydroxide, 6 ml. fractions being collected. Fractions 45–55 contained the desired Compound 5, together with an unknown compound (184 mg. of powder), and fractions 56–86 contained a mixture of Compound 5 and Compound 3 (265 mg. of powder). The latter was dissolved in a 4:5:2:3 mixture of n-butanol:ethanol:chloroform:17% aqueous ammonium hydroxide, the solution was mixed with 1.5 g. of silica gel, and the mixture placed on a 30 g. silica gel column and developed with the same n-butanol:ethanol:chloroform:17% aqueous ammonium hydroxide mixture described above, 5 ml. fractions being collected. Fractions 27–60 contained a mixture of Compound 5 and Compound 3, while the desired Compound 5 was eluted in fractions 61–85. The latter was taken to dryness, and the resulting solid was dissolved in 10 ml. of water. The solution was neutralized with 1 N hydrochloric acid, passed over a column of Amberlite CG-50 (ammonium ion form, 20 ml.), and the column was washed first with 100 ml. of water and then eluted with 0.15 N ammonium hydroxide. Fractions which displayed a single spot on tlc by ninhydrin reagent were combined, concentrated in vacuo and lyophilized to give 60 mg. of 2-hydroxygentamicin $A_3$ (Compound 5) as the carbonate.hydrate, m.p. 202° C., $[\alpha]_D^{20}+109°$ (0.01% in water).

Anal. Calcd. for $C_{18}H_{36}N_4O_{11}.H_2CO_3.H_2O$: C, 40.42; H, 7.14; N, 9.92. Found: C, 40.00; H, 6.40; N, 9.41.

EXAMPLE 1(d)

Purification of Compound 3 (2-Hydroxy Antibiotic JI-20A)

Combined Sample 4 (2500 mg.), consisting of original fractions 28–37 described above, was dissolved in 25 ml. of water, the solution was neutralized with 1 N hydrochloric acid and passed over a column of Amberlite CG-50 resin (ammonium ion form, 125 ml.). The column was washed first with 635 ml. of water and then eluted with 0.15 N ammonium hydroxide, 20 ml. fractions being collected. Thin layer chromatography revealed the presence of impurities in fractions 41–48 and 66–70, and fractions 49–65 were collected, concentrated and lyophilized to give 1460 mg. of Compound 3 as a white amorphous powder. Thin layer chromatographic analysis of the latter revealed the presence of a trace of impurity, and 1450 mg. of the powder were therefore dissolved in 15 ml. of water. The solution was neutralized with 1 N hydrochloric acid, passed over a column of Bio-Rex 63 resin (ammonium ion form, 73 ml.), and the column was washed with 360 ml. of water. The desired compound was then eluted with 0.15 N ammonium hydroxide, 14 ml. fractions being collected. Fractions 61–70 still contained a trace of impurity, and the purified compound was eluted in fractions 71–105, which were combined, concentrated and lyophilized to give 805 mg. of 2-hydroxy antibiotics JI-20A as the carbonate, uncontaminated by impurity (amorphous white powder), m.p. 196° C., $[\alpha]_D^{20}+146°$ (0.01% in water).

Anal. Calcd. for $C_{19}H_{39}N_5O_{10}.H_2CO_3$: C, 42.93; H, 7.38; N, 12.52. Found: C, 42.93; H, 7.01; N, 12.05.

EXAMPLE 1(e)

Purification of Compound 4 (2-Hydroxy Antibiotic JI-20B)

Combined Sample 6 (3600 mg.), derived from original fractions 44–57 described above, was dissolved in 35 ml. of water, and the solution was neutralized with dilute hydrochloric acid and passed over a column of Amberlite CG-50 resin (ammonium ion form, 182 ml.). The column was washed first with 900 ml. of water, and the desired compound was then eluted with 0.15 N ammonium hydroxide, 20 ml. fractions being collected. Fractions 22–61 were combined, concentrated in vacuo and lyophilized to give 3309 mg. of 2-hydroxy antibiotic JI-20B as the hemicarbonate.hemihydrate (white amorphous powder), m.p. 196° C., $[\alpha]_D^{20}+150°$ (0.01% in water).

Anal. Calcd. for $C_{20}H_{41}N_5O_{10}.\frac{1}{2}H_2CO_3.\frac{1}{2}H_2O$: C, 44.64; H, 7.85; N, 12.70. Found: C, 44.80; H, 7.42; N, 12.05.

Further evidence of the structures assigned Compounds 1–5 of the invention was provided by the electron impact (EI) mass spectra of the compounds which were obtained using an Hitachi Model RMU-6MG mass spectrometer. Data so-obtained are given for each of the compounds of the invention in Table 1 below.

TABLE 1

| | | | EI Mass Spectral Data for Compounds 1-5, m/e (% of base peak) | | | | | | | |
|---|---|---|---|---|---|---|---|---|---|---|
| Compound | (MH)+ | M+ | A1 | A2 | A3 | A4 | A5 | A6 | A7 | A8 |
| 1 | 499(1) | 498(1) | 368(59) | 350(4) | 340(30) | | 366(4) | 348(5) | 338(19) | 320(16) |
| 2 | | 512(2) | 382(51) | 364(3) | 354(26) | 336(11) | 366(7) | 348(6) | 338(18) | 320(35) |
| 5 | | 484(1) | 368(4) | | 340(4) | | 352(3) | 334(4) | 324(12) | 306(23) |
| 3 | 498(1) | 497(1) | 367(17) | 349(2) | 339(11) | 321(9) | 366(8) | 348(9) | 338(19) | 320(31) |

TABLE 1-continued

EI Mass Spectral Data for Compounds 1–5, m/e (% of base peak)

| 4 | 512(.5) | 511(1) | 381(21) | | 353(10) | 335(2) | 366(17) | 348(10) | 338(23) | 320(64) |
|---|---|---|---|---|---|---|---|---|---|---|

| Compound | A9 | A10 | A11 | A12 | B1 | C1 | D9 | D10 | D11 | E1 |
|---|---|---|---|---|---|---|---|---|---|---|
| 1 | 207(100) | 189(9)  | 179(60) | 161(43)  | 162(93)  | 160(99)  |         |        | 438(4) | 423(11) |
| 2 | 207(70)  | 189(12) | 179(54) | 161(53)  | 176(100) | 160(100) |         |        | 438(9) | 437(6)  |
| 5 | 207(99)  | 189(14) | 179(51) | 161(38)  | 162(100) | 146(100) |         |        | 424(3) | 423(3)  |
| 3 | 207(41)  | 189(9)  | 179(37) | 161(100) | 161(100) | 160(87)  | 379(5)  | 219(5) |        | 422(3)  |
| 4 | 207(24)  | 189(7)  | 179(29) | 161(32)  | 175(97)  | 160(100) | 378(22) | 219(8) |        | 436(4)  |

| Compound | E2 | E3 | E4 | F1 | F2 | F3 | G1 | G2 |
|---|---|---|---|---|---|---|---|---|
| 1 | 262(10) | 381(23) |         | 307(21) | 305(26) | 146(29) | 118(81) | 100(28) |
| 2 | 276(7)  |         |         | 321(51) | 305(11) |         | 118(81) | 100(28) |
| 5 | 262(12) | 381(11) | 220(34) |         |         |         | 104(51) | 86(75)  |
| 3 | 262(7)  | 380(12) | 220(12) | 306(8)  | 305(13) |         | 118(49) | 100(20) |
| 4 | 262(7)  | 394(14) | 220(6)  | 320(64) | 305(3)  |         | 118(41) | 100(13) |

Assignments of the various structural features of the compounds of the invention based on these data are analogous to, and fully consistent with, assignments from EI mass spectra data reported by Daniels et al., J. Chem. Soc., Perkin I, 1976, 1078–1088; Kugelman et al., ibid, 1976, 1097–1134; and Mallams et al. ibid, 1976, 1135–1146 for various components of gentamicin.

Further evidence of the structural assignments was provided by PMR spectra of the compounds which were obtained in $D_2O$ using a JEOL Model JNM-MH-100 nmr spectrometer as follows:

| | δ (ppm) | Assignment |
|---|---|---|
| Compound 1: | 1.24 | 4″-C—$CH_3$ |
|  | 2.66 | 3″-N—$CH_3$ |
|  | 5.08, 5.26 | Two anomeric protons |
| Compound 2: | 1.24 | 4″-C—$CH_3$ |
|  | 1.2–1.3 | 6′-C—$CH_3$ |
|  | 2.64 | 3″-N—$CH_3$ |
|  | 5.08, 5.35 | Two anomeric protons |
| Compound 3: | 1.26 | 4″-C—$CH_3$ |
|  | 2.70 | 3″-N—$CH_3$ |
|  | 5.13, 5.22 | Two anomeric protons |
| Compound 4: | 1.26 | 4″-C—$CH_3$ |
|  | 1.2–1.3 | 6′-C—$CH_3$ |
|  | 2.58 | 3″-N—$CH_3$ |
|  | 5.07, 5.30 | Two anomeric protons |
| Compound 5: | 2.64 | 3″-N—$CH_3$ |
|  | 5.06, 5.30 | Two anomeric protons |

Finally, acid hydrolysis of the compounds of the invention and tlc analysis of the degradation products served to confirm the presence of certain assigned structural features of the compounds as follows:

Acid hydrolysis of Compound 1 produced four products which, on tlc analysis, were positive to silver nitrate reagent, three of which were positive to ninhydrin reagent. The product which was positive to silver nitrate but negative to ninhydrin had the same $R_f$ value as the garosamine moiety (i.e. the O-[3-deoxy-4-C-methyl-3-methylamino-β-L-arabinopyranosyl]-group) produced by acid hydrolysis of hydroxygentamicins $C_1$, $C_2$ and $C_{1a}$. The second product had the same $R_f$ value as D-streptamine and 2-deoxystreptamine, while the third and fourth products were found to correspond, on tlc analysis, to 6-amino-6-deoxyglucose and its further degradative product which were obtained from the hydrolysis of kanamycin.

Compound 2, on acid hydrolysis, produced four products which, on tlc analysis, were positive to silver nitrate reagent, three of which were positive to ninhydrin reagent. The product which was positive to silver nitrate but negative to ninhydrin and one of the products that was positive to both silver nitrate and ninhydrin were assigned the garosamine and D-streptamine moieties, respectively, on the same basis as the assignments in the case of Compound 1. The other two products which were positive to both silver nitrate and ninhydrin showed a higher chromatographic mobility in comparison with 6-amino-6-deoxyglucose and its further degradation product, and these two products were assigned as having been derived from the 6-amino-6-C-methyl-6-deoxyglucose moiety and its further degradation product, by analogy with the gentamicins where the components having a C-methyl group in the 6-amino-6-deoxyglucose moiety show similar chromatographic behavior.

Compound 3, on acid hydrolysis, produced only two products, one having the same $R_f$ value as garosamine and the other having an $R_f$ value similar to neamine. The latter fragment was assigned as being a pseudo-disaccharide which was not hydrolyzed with acid because of the presence of an amino group at the 2′-position of the 2,6-dideoxyglucose moiety.

Compound 5, on acid hydrolysis, produced only two products, one having the same $R_f$ value as garosamine and the other showing a higher chromatographic mobility in comparison with neamine. The latter fragment was assigned as the C-methylated derivative of the fragment which was found in Compound 3.

D. Preparation of the
1-N-(ω-Amino-α-hydroxylower-alkanoyl) Derivatives

EXAMPLE 2

In two separate runs, a solution containing a total of 890 mg. of O-[3-deoxy-4-C-methyl-3-methylamino-β-L-arabinopyranosyl-(1→6)]-O-[6-amino-6-deoxy-α-D-erythroglucopyranosyl-(1→4)]-D-streptamine (2-hydroxygentamicin B) dissolved in a total of 10 ml. of water containing 660 mg. of triethylamine was treated dropwise, with stirring at 5° C., with a total of 395 mg. of t-butyl S-(4,6-dimethylpyrimidin-2-yl) thiolcarbonate in a total of 10 ml. of dioxane, and the solution was stirred at 5° C. for twenty-four hours and then treated with another 27 mg. of the t-butyl thiolcarbonate reagent and stirred for an additional seventy-two hours at 5° C. The mixture was then taken to dryness in vacuo, and the residue was dissolved in methanol and placed on three thick layer silica gel chromatography plates and developed using the lower phase of a 2:1:1 mixture of chloroform:methanol:concentrated ammonium hydroxide. There was thus obtained a total of 637 mg. of O-[3-deoxy-4-C-methyl-3-methylamino-β-L-arabinopyranosyl-(1→6)]-O-[6-(t-butoxycarbonyl- )amino-6-deoxy-α-D-erythro-glucopyranosyl-(1→4)]-D-streptamine as the more polar component ($R_f$ 0.1 on Whatman MK6F silica gel plates developed using the lower phase of a 2:1:1 mixture of chloroform:methanol:concentrated ammonium hydroxide.) (All $R_f$ values recorded hereinafter were obtained in the same system just described.)

The nmr spectrum (obtained, in this and all other cases subsequently recorded herein, in $D_2O$ on a 60 MHz PMR spectrometer using sodium 2,2-dimethyl-2-silapentan-5-sulfonate as internal standard) showed peaks at 1.21 ppm (three C-$CH_3$ protons of the 4″-C-$CH_3$ group); 1.43 ppm (nine protons of the t-butyl group); 2.53 ppm (three protons of the 3″-N-$CH_3$ group); and 5.08(d) and 5.18(d) ppm (two anomeric protons).

The latter (620 mg.) was dissolved in 24 ml. of a 1:3 solution of methanol in water, and the solution was cooled to 5° C. and treated dropwise, with stirring at 5° C., with a solution of 356 mg. of the N-hydroxysuccinimide ester of S-(−)-γ-(benzyloxycarbonyl)amino-α-hydroxybutyric acid (Konishi et al., U.S. Pat. No. 3,780,018) in 5 ml. of dimethylformamide. The solution was stirred for an additional three hours at 5° C., taken to dryness in vacuo, and the residue was dissolved in methanol and developed on five thick layer silica gel chromatography plates using the lower phase of a 2:1:1 mixture of chloroform:methanol:concentrated ammonium hydroxide. There was thus obtained two components, the first comprising 550 mg. of a more polar component ($R_f$ 0.1) and the second comprising 70 mg. of a less polar component ($R_f$ 0.24). The more polar component was treated again with an additional 316 mg. of the N-hydroxysuccinimide ester of S-(−)-γ-(benzyloxycarbonyl)amino-α-hydroxybutyric acid using the procedure described above, and the product was worked up as before and chromatographed on four thick layer chromatography plates to give an additional 70 mg. of the same less polar component ($R_f$ 0.24) consisting of 1-[S-(−)-γ-(benzyloxycarbonyl)amino-α-hydroxybutyryl]-O-[3-deoxy-4-C-methyl-3-methylamino-β-L-arabinopyranosyl-(1→6)]-O-[6-(t-butoxycarbonyl)amino-6-deoxy-α-D-erythro-glucopyranosyl-(1→4)]-D-streptamine.

The nmr spectrum of the latter showed peaks at 1.32 ppm (three C-$CH_3$ protons of the 4″-C-$CH_3$ group); 1.44 ppm (nine protons of the t-butyl group); 2.09(m) and 3.04(m) ppm (four $CH_2CH_2$ protons of the γ-amino-α-hydroxybutyryl group); 2.78 ppm (three protons of the 3″-N-$CH_3$ group); 5.10 ppm (two methylene protons of the $C_6H_5CH_2O$ group); and 7.40(m) ppm (five protons of the $C_6H_5$ group).

The latter (140 mg.) dissolved in 25 ml. of a 50% methanol:water solution, was reduced with hydrogen over 100 mg. of 10% palladium-on-charcoal under 50 pounds p.s.i.g. When reduction was complete, the catalyst was removed by filtration, the filtrate was taken to dryness in vacuo, and the residue (102 mg.) was dissolved in methanol and developed on a thick layer silica gel plate using the lower phase of a 2:1:1 mixture of chloroform:methanol:concentrated ammonium hydroxide. The more polar band was scraped from the plate, the product was recovered in the same mixed solvent system, and the solution was evaporated to dryness to give 63 mg. of 1-[S-(−)-γ-amino-γ-hydroxybutyryl]-O-[3-deoxy-4-C-methyl-3-methylamino-β-L-arabinopyranosyl-(1→6)]-O-[6-(t-butoxycarbonyl)amino-6-deoxy-α-D-erythro-glucopyranosyl-(1→4)]-D-streptamine. ($R_f$ 0.07).

The nmr spectrum of the latter showed peaks at 1.25 ppm (three C-$CH_3$ protons of the 4″-C-$CH_3$ group); 1.41 ppm (nine protons of the t-butyl group); 2.09(m) and 3.04(m) ppm (four $CH_2CH_2$ protons of the γ-amino-α-hydroxybutyryl group); 2.70 ppm (three protons of the 3″-N-$CH_3$ group); and 5.08(d) and 5.18(d) ppm (two anomeric protons).

The latter (58 mg.) was dissolved in 0.4 ml. of trifluoroacetic acid, and the solution was allowed to stand at ambient temperature for five minutes. The solution was then diluted with 30 ml. of diethyl ether, and the solid which separated was collected and dried to give 65.7 mg. of 1-[S-(−)-γ-amino-α-hydroxybutyryl]-O-[3-deoxy-4-C-methyl-3-methylamino-β-L-arabinopyranosyl-(1→6)]-O-[6-amino-6-deoxy-α-D-erythro-glucopyranosyl-(1→4)]-D-streptamine, as the trifluoroacetate.nonahydrate.

Anal. Calcd. for $C_{23}H_{45}N_5O_{13}$·$3CF_3COOH$·$9H_2O$: C, 31.55; H, 6.03; N, 6.34; F, 15.5. Found: C, 31.41; H, 5.42; N, 5.85; F, 15.65.

The nmr spectrum of the sample showed peaks at 1.31 ppm (three C-$CH_3$ protons of the 4″-C-$CH_3$ group); 2.89 ppm (three N-$CH_3$ protons of the 3″-N-$CH_3$ group); 2.09 and 3.49 ppm (four $CH_2CH_2$ protons of the γ-amino-α-hydroxybutyryl group); and 5.17 and 5.54 ppm (two anomeric protons).

EXAMPLE 3

It is contemplated that, by following a procedure similar to that described above in Example 2, O-[3-deoxy-4-C-methyl-3-methylamino-β-L-arabinopyranosyl-(1→6)]-O-[6-amino-6-C-methyl-6-deoxy-α-D-erythro-glucopyranosyl-(1→4)]-D-streptamine can be reacted with t-butyl S-(4,6-dimethylpyrimidin-2-yl) thiolcarbonate in the presence of triethylamine to afford O-[3-deoxy-4-C-methyl-3-methylamino-β-L-arabinopyranosyl-(1→6)]-O-[6-(t-butoxycarbonyl)amino-6-C-methyl-6-deoxy-α-D-erythro-glucopyranosyl-(1→4)]-D-streptamine, which on reaction with the N-hydroxysuccinimide ester of S-(−)-β-(benzyloxycarbonyl)amino-α-hydroxypropionic acid, would afford 1-[S-(−)-β-(benzyloxycarbonyl)amino-α-hydroxypropionyl]-O-[3-deoxy-4-C-methyl-3-methylamino-β-L-arabinopyranosyl-(1→6)]-O-[6-(t-butoxycarbonyl)amino-6-C-methyl-6-deoxy-α-D-erythro-glucopyranosyl-(1→4)]-D-streptamine, which on catalytic reduction over palladium-on-charcoal under a hydrogen pressure of about 50 pounds p.s.i.g., would afford 1-[S-(−)-β-amino-α-hydroxypropionyl]-O-[3-deoxy-4-C-methyl-3-methylamino-β-L-arabinopyranosyl-(1→6)]-O-[6-(t-butoxycarbonyl)amino-6-C-methyl-6-deoxy-α-D-erythroglucopyranosyl-(1→4)]-D-streptamine, which on reaction with trifluoroacetic acid would afford 1-[S-(−)-β-amino-α-hydroxypropionyl]-O-[3-deoxy-4-C-methyl-3-methylamino-β-L-arabinopyranosyl-(1→6)]-O-[6-amino-6-C-methyl-6-deoxy-α-D-erythro-glucopyranosyl-(1→4)]-D-streptamine, i.e. the 1-N-(β-amino-α-hydroxypropionyl) derivative of 2-hydroxygentamicin $B_1$.

BIOLOGICAL TEST RESULTS

The antibacterial activity of the compounds of the invention was demonstrated by antibacterial tests in vitro against a variety of microorganisms using a standard serial dilution method. The results, expressed in terms of the minimum inhibitory concentration (MIC, γ/ml.), are given in Table 2 below. For reference purposes, corresponding data are included, where available, for the 2-hydroxygentamicin $C_1$, $C_2$, $C_{1a}$ complex. The abreviations 1-HABA and HOGM represent the 1-N-(γ-amino-α-hydroxybutyryl) derivative of Compound 1 and 2-hydroxygentamicin $C_1$, $C_2$, $C_{1a}$ complex, respectively.

TABLE 2

| Microorganism | Compound 1 | 2 | 3 | 4 | 5 | Cpd. 1(1-HABA) | HOGM |
|---|---|---|---|---|---|---|---|
| Staph. aureus 209P | 3.12 | 3.12 | 0.78 | 1.56 | 12.5 | — | 1.56 |
| Staph. aureus Smith | 3.9 | — | — | — | — | 3.9 | — |
| Staph. aureus Giorgio | 15.6 | — | — | — | — | 15.6 | — |
| Staph. aureus BH-2 | — | — | — | — | — | 31 | 31.3 |
| B. subtilis ATCC 6633 | 0.39 | 0.78 | 0.2 | 0.39 | 3.12 | — | 0.2 |
| E. coli NIHJ | 3.12 | 3.12 | 1.56 | 1.56 | 12.5 | — | 1.56 |
| E. coli K-12 ML 1629 | 25 | 6.25 | 100 | 50 | >100 | — | 1.56 |
| E. coli K-12 (CS-2) | 0.78 | 0.78 | 0.39 | 0.78 | 6.25 | — | 0.78 |
| E. coli Vogel | 7.8 | — | — | — | — | 7.8 | — |
| E. coli JR 88 | — | — | — | — | — | 3.9 | 31.3 |
| E. coli JR 225 | — | — | — | — | — | 15.6 | 125 |
| K. pneumoniae 602 | 3.12 | 3.12 | 1.56 | 1.56 | 12.5 | — | 1.56 |
| K. pneumoniae 39645 | 3.9 | — | — | — | — | 3.9 | — |
| K. pneumoniae A 20636 | — | — | — | — | — | 7.8 | 6.25 |
| Ps. aeruginosa IAM 1007 | 12.5 | 6.25 | 25 | 12.5 | >100 | — | >3.12 |
| Ps. aeruginosa MGH-2 | 7.8 | — | — | — | — | 3.9 | — |
| Salmonella paratyphi A | 3.12 | 1.56 | 0.78 | 0.78 | 6.25 | — | 0.78 |
| Prot. vulgaris | 0.78 | 1.56 | 0.39 | 0.39 | 3.12 | — | 0.39 |
| Prot. vulgaris 9920 | 15.6 | — | — | — | — | 15.6 | — |
| Prot. mirabilis MGH-1 | 15.6 | — | — | — | — | 15.6 | — |
| Strep. pyogenes C 203 | 31.3 | — | — | — | — | 62.5 | — |
| C. albicans 10231 | >62.5 | — | — | — | — | >125 | — |
| A. niger 16404 | >62.5 | — | — | — | — | >125 | — |
| T. mentagrophytes 9129 | >62.5 | — | — | — | — | >125 | — |

We claim:

1. A member of the group consisting of (A) a compound having one of the formulas:

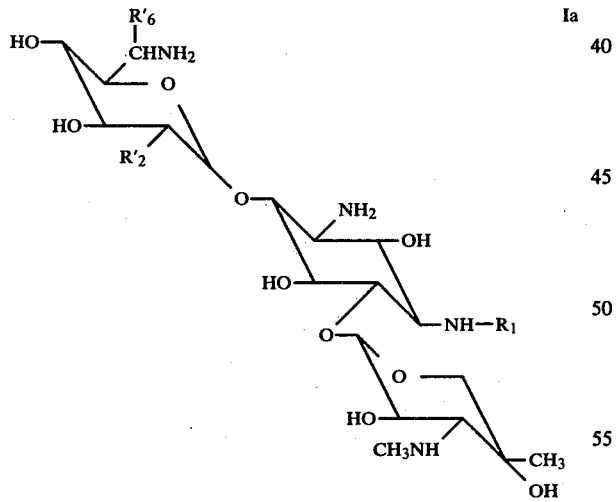

Ia

-continued or

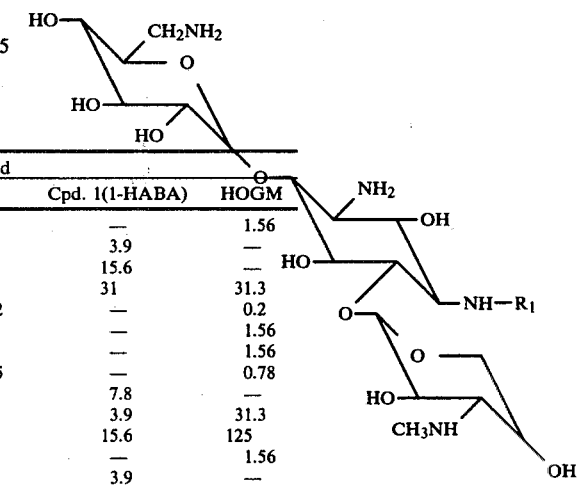

Ib where $R_1$ is hydrogen or an ω-amino-α-hydroxy-lower-alkanoyl group, $H_2N(CH_2)_nCHOHCO-$, where n is one of the integers 1 or 2; and where, in formula Ia, $R_2'$ is hydroxy or amino and $R_6'$ is hydrogen or methyl; and (B) acid-addition salts thereof.

2. 2-Hydroxygentamicin B according to claim 1.
3. 2-Hydroxygentamicin $B_1$ according to claim 1.
4. 2-Hydroxy antibiotic JI-20A according to claim 1.
5. 2-Hydroxy antibiotic JI-20B according to claim 1.
6. 2-Hydroxygentamicin $A_3$ according to claim 1.

* * * * *